(12) United States Patent
Kim et al.

(10) Patent No.: US 10,057,451 B2
(45) Date of Patent: Aug. 21, 2018

(54) ASTRAL LAMP DEVICE HAVING DETACHABLE AND ANGLE-CONTROLLABLE LED MODULE BLOCKS AND METHOD OF SETTING THE SAME

(71) Applicant: ELECTRONICS AND TELECOMMUNICATIONS RESEARCH INSTITUTE, Daejeon (KR)

(72) Inventors: Jeong Eun Kim, Gwangju (KR); Hyun Seo Kang, Gwangju (KR); Hyoung Jun Park, Gwangju (KR); Dae Won Choi, Gwangju (KR); Jai Sang Koh, Gwangju (KR); Keo Sik Kim, Gwangju (KR); Young Sun Kim, Gwangju (KR); Ji Hyoung Ryu, Jeonju (KR); Kwon Seob Lim, Gwangju (KR); Eun Kyoung Jeon, Gwangju (KR); Young Soon Heo, Gwangju (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 367 days.

(21) Appl. No.: 14/869,573

(22) Filed: Sep. 29, 2015

(65) Prior Publication Data
US 2016/0097518 A1 Apr. 7, 2016

(30) Foreign Application Priority Data
Oct. 1, 2014 (KR) .......................... 10-2014-0132574

(51) Int. Cl.
*H04N 1/21* (2006.01)
*G03B 15/14* (2006.01)
(Continued)

(52) U.S. Cl.
CPC ............ *H04N 1/2112* (2013.01); *A61B 90/30* (2016.02); *F21S 2/005* (2013.01); *F21V 14/02* (2013.01);
(Continued)

(58) Field of Classification Search
CPC .......... A61B 90/30; F21S 2/005; F21V 14/02; F21V 21/14; F21V 21/26; F21V 21/30;
(Continued)

(56) References Cited

U.S. PATENT DOCUMENTS 5,951,139 A 9/1999 Smith et al.
7,465,065 B2 12/2008 Marka
(Continued)

FOREIGN PATENT DOCUMENTS

KR 10-1041414 6/2011
KR 10-1109473 1/2012
(Continued)

*Primary Examiner* — Stephen F Husar (57) ABSTRACT

Disclosed herein are an astral lamp device having detachable and angle-controllable LED module blocks and a method of setting the same. The astral lamp device having detachable and angle-controllable LED module blocks, includes a plurality of LED module blocks having one end attached to and disposed on a central frame; and an angle control part configured to control an angle of the LED module block attached to the central frame.

15 Claims, 8 Drawing Sheets

(51) Int. Cl.
    *G03B 15/02*     (2006.01)
    *F21V 21/30*     (2006.01)
    *F21V 21/26*     (2006.01)
    *F21V 21/14*     (2006.01)
    *F21S 2/00*     (2016.01)
    *F21V 14/02*     (2006.01)
    *A61B 90/30*     (2016.01)
    *F21W 131/20*     (2006.01)
    *F21W 131/205*     (2006.01)
    *F21Y 115/10*     (2016.01)

(52) U.S. Cl.
    CPC .............. *F21V 21/14* (2013.01); *F21V 21/26* (2013.01); *F21V 21/30* (2013.01); *G03B 15/02* (2013.01); *G03B 15/14* (2013.01); *F21W 2131/20* (2013.01); *F21W 2131/205* (2013.01); *F21Y 2115/10* (2016.08); *G03B 2215/0567* (2013.01)

(58) Field of Classification Search
    CPC ......... F21W 2131/20; F21W 2131/205; F21Y 2115/10; G03B 15/02; G03B 15/14; G03B 2215/0567; H04N 1/2112

USPC .............................................. 362/11, 249.03
See application file for complete search history.

(56) References Cited

U.S. PATENT DOCUMENTS

| | | | |
|---|---|---|---|
| 7,832,901 B2 * | 11/2010 | Ladewig | F21S 2/005 362/227 |
| 8,317,361 B2 | 11/2012 | Lee | |
| 8,737,731 B2 | 5/2014 | Park et al. | |
| 2011/0170288 A1 * | 7/2011 | Kim | F21V 21/30 362/235 |
| 2012/0016290 A1 | 1/2012 | Shin | |
| 2012/0147604 A1 * | 6/2012 | Farmer | H05B 37/0254 362/249.03 |
| 2013/0329451 A1 | 12/2013 | Lin et al. | |

FOREIGN PATENT DOCUMENTS

| | | |
|---|---|---|
| KR | 10-2012-011691 | 2/2012 |
| KR | 20-2012-0005974 U | 8/2012 |
| KR | 20-2013-0005491 U | 9/2013 |
| KR | 10-2014-0000914 A | 1/2014 |

* cited by examiner

ASTRAL LAMP DEVICE HAVING DETACHABLE AND ANGLE-CONTROLLABLE LED MODULE BLOCKS AND METHOD OF SETTING THE SAME

CROSS-REFERENCE TO RELATED APPLICATION

This application claims priority to and the benefit of Korean Patent Application No. 10-2014-0132574, filed on Oct. 1, 2014, the disclosure of which is incorporated herein by reference in its entirety.

BACKGROUND

1. Field of the Invention

The present invention relates to an astral lamp device having a light emitting diode (LED) capable of excellently illuminating a wound for surgery or diagnosis and a method of setting the same.

2. Discussion of Related Art

Astral lamps are lighting instruments configured to illuminate a wound during surgery in a hospital and/or the like.

The astral lamps include a one lamp type, a multi lamp type, and/or the like, and have a high luminance and color rendering index, and prevents radiant heat and the shadow of a hand.

The above astral lamps are medical instruments necessary for medical staffs to perform a procedure in a surgery at an optimum state.

Conventional light emitting diode (LED) astral lamps have a longer lifetime and lower power consumption than astral lamps using a conventional halogen lamp and a xenon lamp.

Also, since heat radiation on a front part thereof is nearly nonexistent, the LED astral lamps increase the degree of concentration of the medical staff during a procedure, and have a benefit of preventing desiccation of a tissue and blood by the radiant heat.

Also, since the conventional LED astral lamps excellently express the original colors of an object by a high color rendering in, precise diagnosis of a wound is possible.

Thus, a more precise surgery is possible, and an ultraviolet wavelength which harmfully affects the wound is not generated.

Thus, the conventional LED astral lamps have many benefits compared with the conventional astral lamps and general lightings with respect to the convenience in the surgical environment, but have a high price, and thus, are mainly used in a general hospital in which a human patient is treated.

Only some large animal hospitals use astral lamps for a general medical purpose, but developing countries or backward regions with poor medical facilities and middle or small sized animal hospitals use general deck working, lamps or stand-type lightings of low price due to the financial burden, but the above lightings have problems of a short lifetime, high power consumption, and heat generation.

SUMMARY OF THE INVENTION

The present invention is directed to providing an astral lamp device having light emitting diode (LED) module blocks capable of controlling, the number of the LED module blocks based on the economic or environmental circumstances of a user, and controlling angles of the LED module blocks based on a size of a wound to control light illumination range.

According to an aspect of the present invention, there is provided low-cost and customized LED astral lamp device replacing general lightings used in developing countries or backward regions with poor medical facilities, and middle or small sized animal hospitals.

According to an aspect of the present invention, there is provided an astral lamp device having detachable and angle-controllable LED module blocks, including a plurality of LED module blocks having one ends attached to and disposed on a central frame, and an angle control part configured to control an angle of each LED module blocks attached to the central frame.

According to another aspect of the present invention, there is provided a method of setting an astral lamp device having detachable and angle-controllable LED module blocks, including attaching one ends of a plurality of LED module blocks to a central flame, and controlling an angle of each LED module block.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, exemplary embodiments of the present invention will be described in detail with reference to the accompanying drawings. In the following description and the appended drawings, detailed descriptions of well-known functions or constructions will be omitted if they obscure the invention with unnecessary detail. Also, the present invention may be embodied in different forms and should not be construed as limited to the embodiments set forth herein.

The exemplary embodiments described herein are only provided so as a skilled person in the art of the present invention can embody the inventive concept of the present invention. The terms used in the present invention are only used to describe particular embodiments, and are not intended to limit the present invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, best modes of the present invention will be described in detail with reference to the accompanying drawings. In numbering reference numerals to the structural parts of each drawing, like numerals may refer to like elements throughout the description of the figures although the reference numerals are displayed in different drawings.

Figure 1:
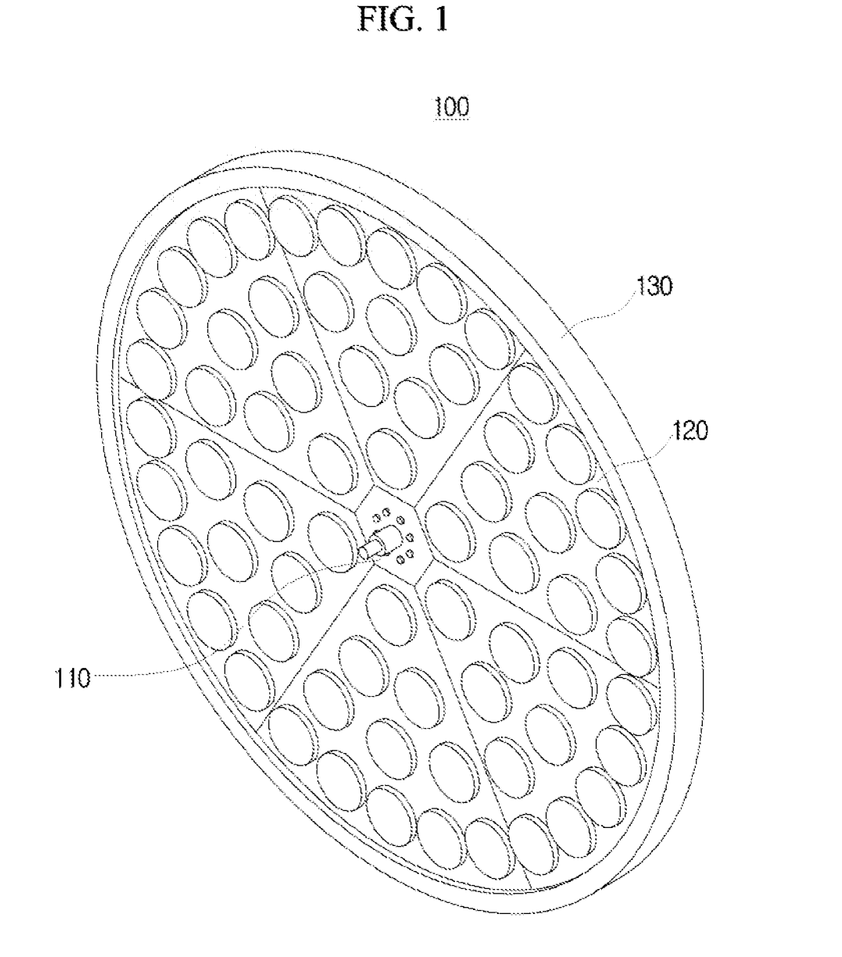
FIG. 1 is a view illustrating a head structure of an astral lamp device according to an embodiment of the present invention.
Figure 2:
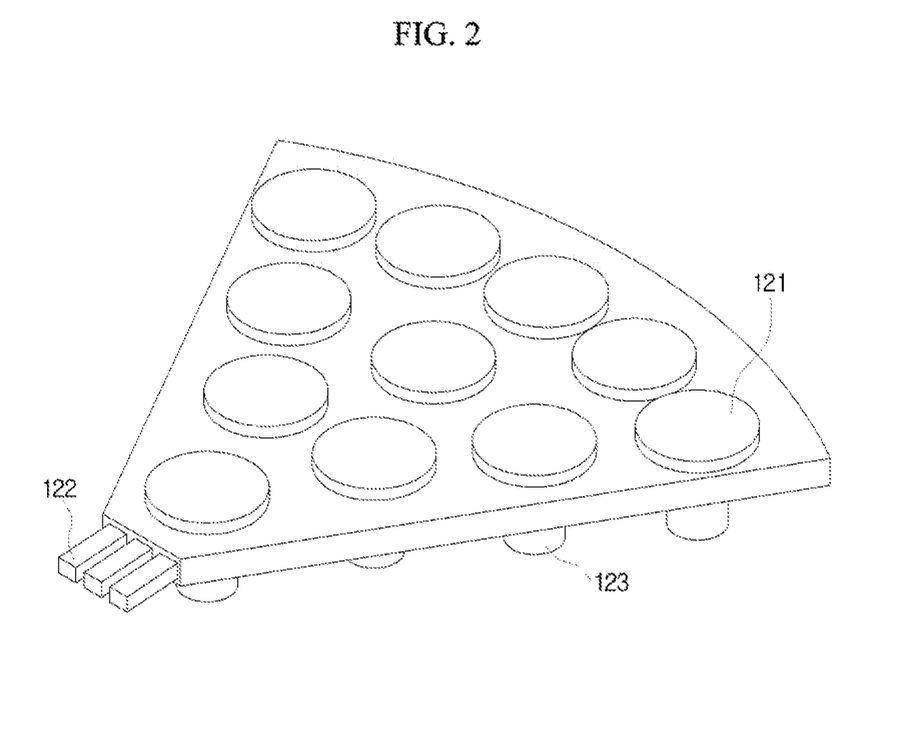
FIG. 2 is a perspective view illustrating a structure of a light emitting diode (LED) module block according to the embodiment of the present invention.

FIG. 1 is a view illustrating a head structure of an astral lamp device according to an embodiment of the present invention, and FIG. 2 is a perspective view illustrating a structure of a light emitting diode (LED) module block according to the embodiment of the present invention.

This is one example for describing the embodiment of the present invention, and a shape of the light emitting diode (LED) module block of the present invention is not limited to sector shape (it could be quadrangle or others).

Referring to FIGS. 1 and 2, an astral lamp device 100 using LED module blocks according the embodiment of the present invention may be detachable using a detachable interface 122 with respect to a central frame 110 of the astral lamp device 100, and includes LED module blocks 120 in which individual heat dissipation parts 123 are formed.

The plurality of LED module blocks 120 each includes one end attached to the central frame 110 and an angle control part configured to control an angle of the LED module block 120.

The angle control part according to the embodiment of the present invention will be described below in detail with reference to FIGS. 5 and 6.

As illustrated in FIG. 2, the LED module block 120 according to the embodiment of the present invention is a detachable block, and includes the detachable interface 122 configured to connect the central frame 110 to the LED module block 120, at least one LED module 121, and the heat dissipation part 123 of the LED module 121.

That is, each of the LED module blocks 120 is configured to include at least one LED module 121, and the detachable interface 122 to be connected to the central frame 110 (a basic flame) is provided in each LED module block 120, and includes the heat dissipation part 123 with respect to each of the LED module blocks 120 to dissipate heat during attaching/detaching of the LED module block 120.

Here, the detachable interface 122, as illustrated in FIG. 2, may preferably be a pin shaped interface configured to connect the LED module block 120 to the central frame 110, but this is one example for describing the embodiment of the present invention, and a shape of the detachable interface of the present invention is not limited to the pin shape.

Also, the heat dissipation part 123 according to the embodiment of the present invention, as illustrated in FIG. 2, may be disposed on a surface opposite a surface on which the LED module 121 is disposed.

The astral lamp device using the LED module block according to the embodiment of the present invention may further include an outer frame 130 which forms an outer circumference and is connected to the other end of the LED module block 120 to support the LED module block 120.

The LED module blocks according to the exemplary embodiment of the present invention respectively include individual dimming systems which are directly connected to 220 V alternating current (AC), and thus, provide a function of controlling the luminance of the LED astral lamp device based on the circumstances of a surgery.

Figure 3:
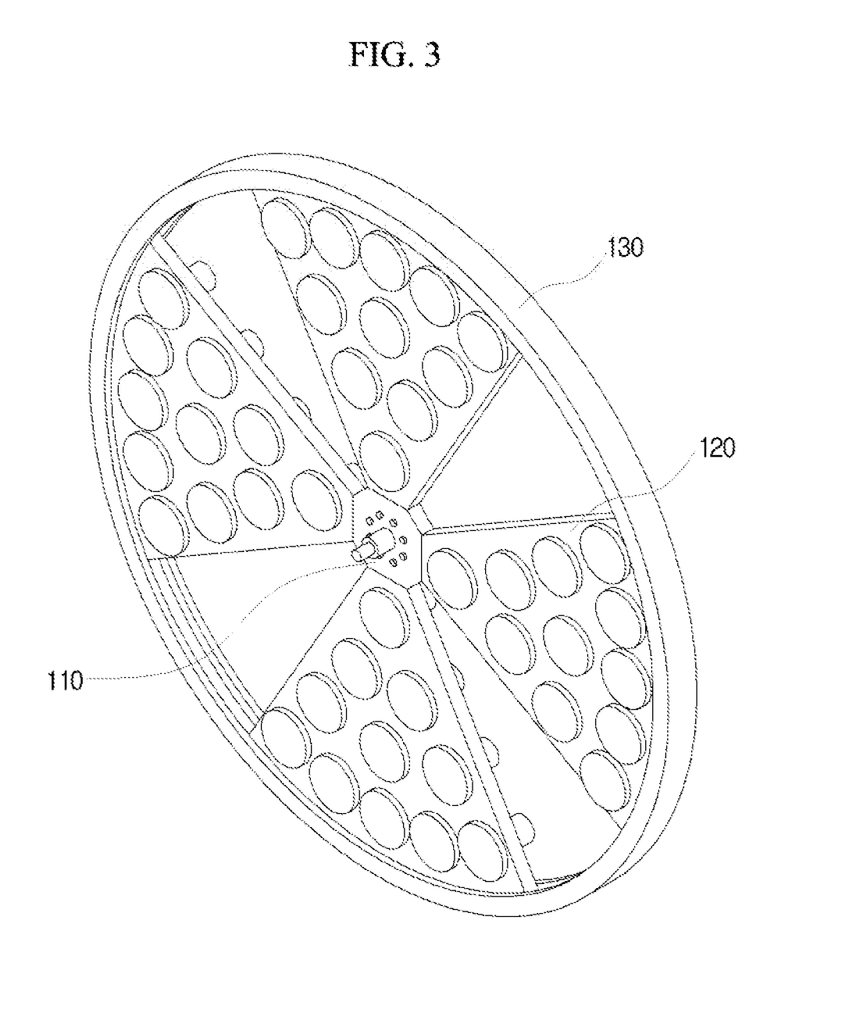
FIG. 3 is a view illustrating the astral lamp device in which four LED module blocks are attached according to the embodiment of the present invention.
Figure 4:
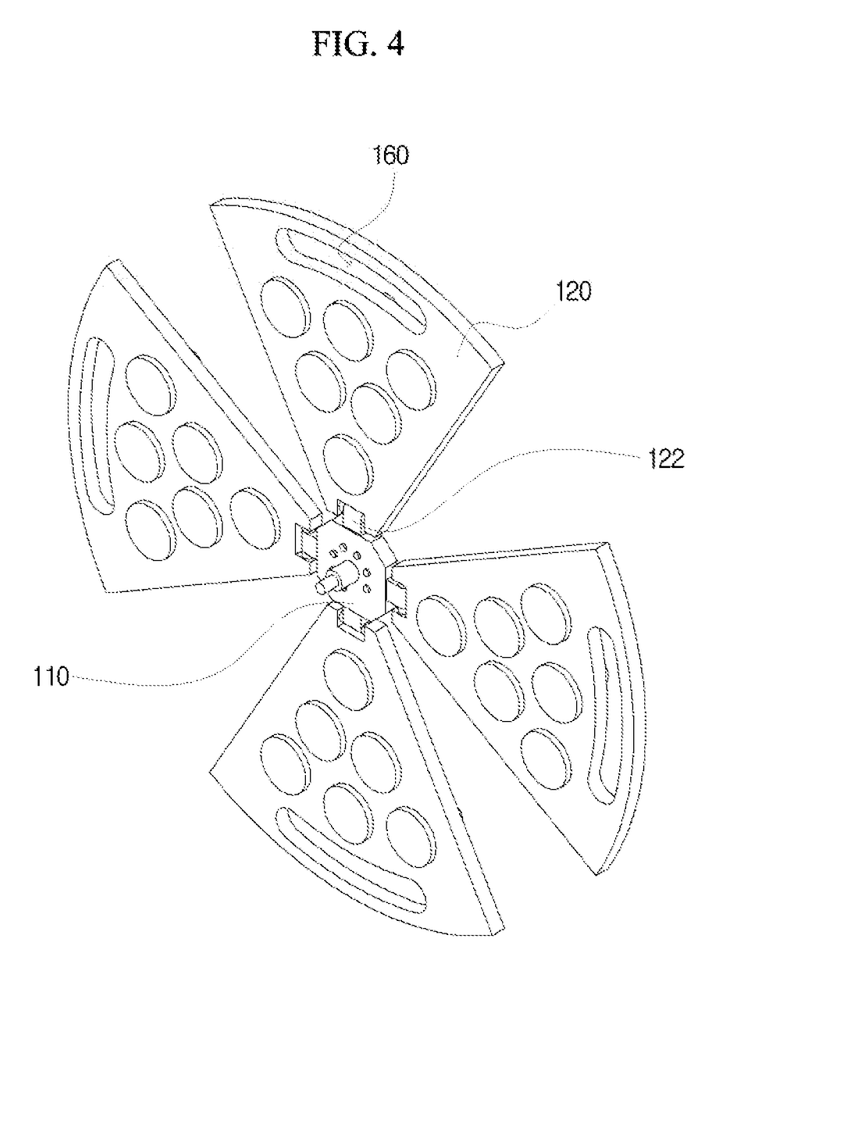
FIG. 4 is a view illustrating a head structure of an astral lamp device according to an embodiment of the present invention another embodiment of the present invention.

FIG. 3 is a view illustrating the astral lamp device in which four LED module blocks are attached according to the embodiment of the present invention and FIG. 4 is a conceptual view illustrating stabilizer switching of the astral lamp device in which the four LED module blocks are attached according to the embodiment of the present invention.

The LED astral lamp device according to the embodiment of the present invention further includes a switching part 140 configured to switch to a stabilizer 143 of preset wattage based on the number of the LED module blocks 120 attached to the central frame 110.

Figure 5:
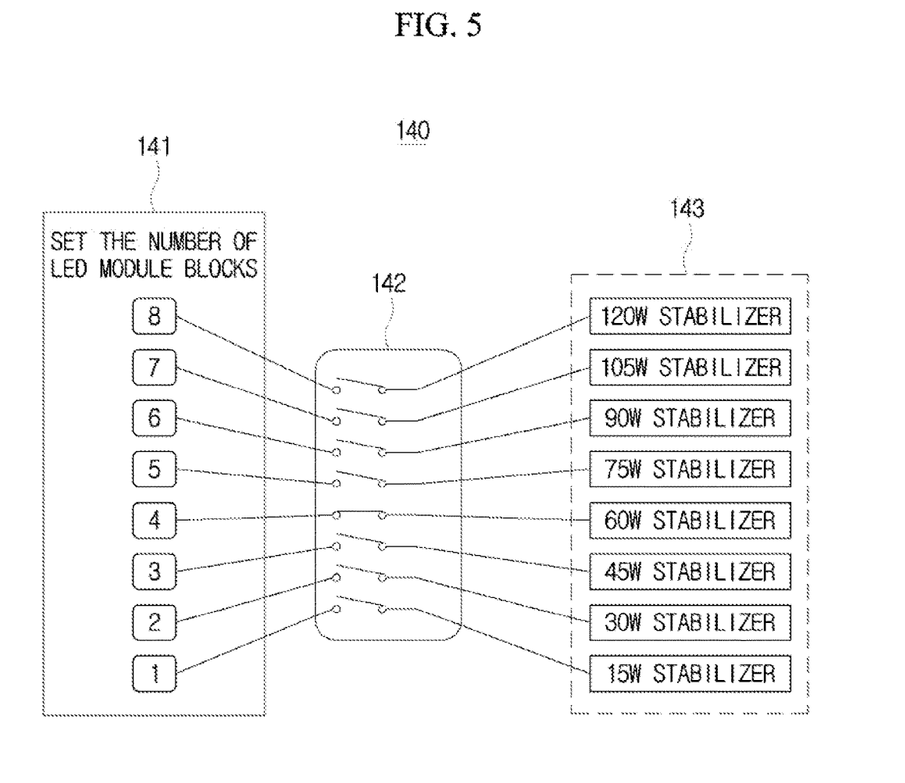
FIG. 5 is a conceptual view illustrating stabilizer switching of the astral lamp device in which the four LED module blocks are attached according to the embodiment of the present invention.

The switching part 140 according to the embodiment of the present invention, as illustrated in FIG. 5, includes a setting part 141, the stabilizer 143, and a switch 142 configured to connect the setting part 141 to the stabilizer 143.

As illustrated in FIG. 3, in an example where four LED module blocks are attached, the setting part 141 according to the embodiment of the present invention receives a setting signal of four which is the number of the attached LED module blocks 120 and transmits a switching signal based on the above, and when one LED module block is 15 W, the stabilizer is switched to a 60 W stabilizer among stabilizers (a 15 W stabilizer, a 30 W stabilizer, a 45 W stabilizer, the 60 W stabilizer, a 75 W stabilizer, a 90 W stabilizer, a 105 W stabilizer, and a 120 W stabilizer) which corresponds to the four LED module blocks.

That is, the switching part 140 according to the embodiment of the present invention switches to a stabilizer 143 corresponding to a change in output by the change in the number of the LED module blocks, and thus, convenience for a user is increased.

The LED astral lamp device according to the embodiment of the present invention may individually include the stabilizer at each individual LED module block, and thus, may attach/detach the LED module block on/from the central frame without the above switching process.

In this case, the additional setting signal input is not necessary, and the individual stabilizer may operate by only attaching/detaching the LED module block on/from the central frame, and thus, the additional switching process may be omitted.

In another embodiment. FIG. 4 is a view illustrating a head structure of an astral lamp device according to an embodiment of the present invention another embodiment of the present invention.

As mentioned above, the detachable interface 122 has another shape as illustrated in FIG. 4, and angle of LED module block 120 may be controlled by angle control lever 160.

Users may manually push or pull the angel control lever 160 connected to each LED module block 120, so that the angle of the LED module block may be controlled.

Figure 6:
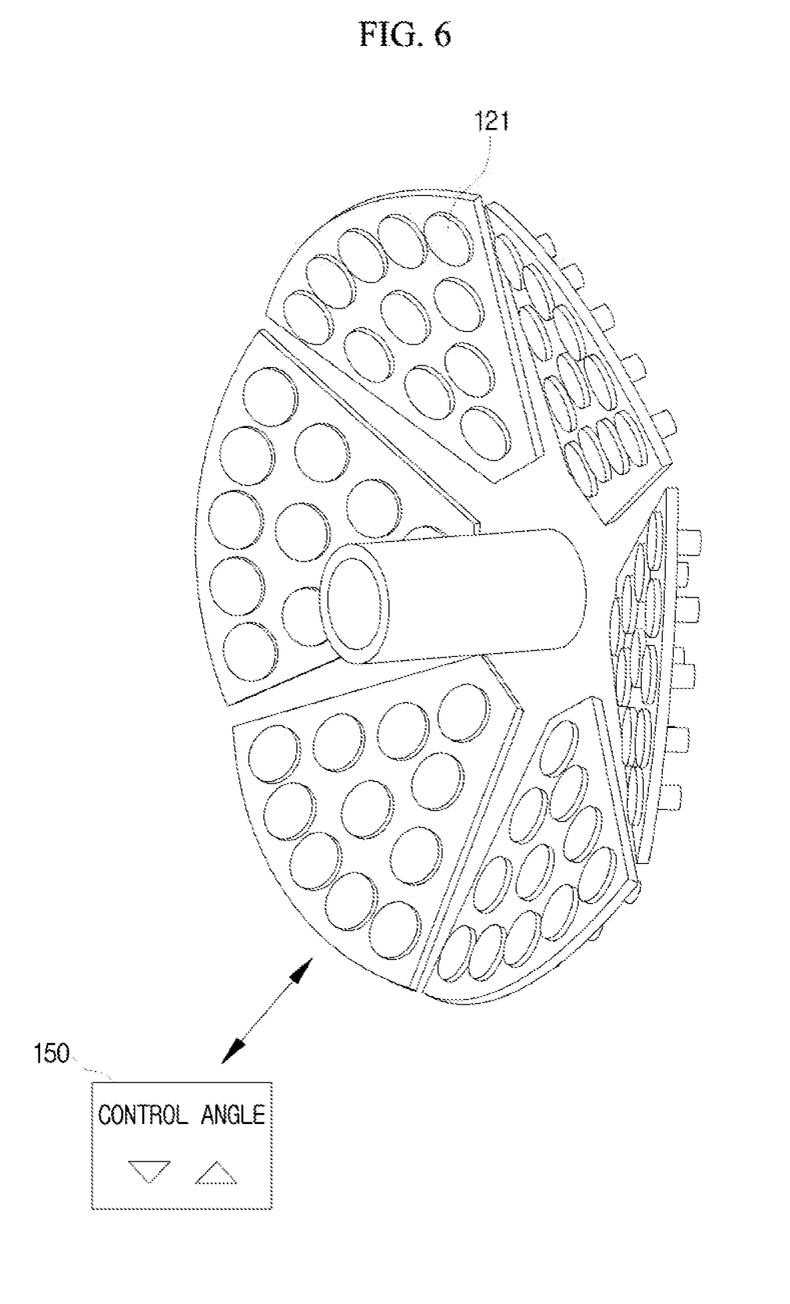
FIG. 6 is an exemplary view illustrating a state in which an angle of the LED module block of the astral lamp device according to the embodiment of the present invention is controlled.
Figure 7:
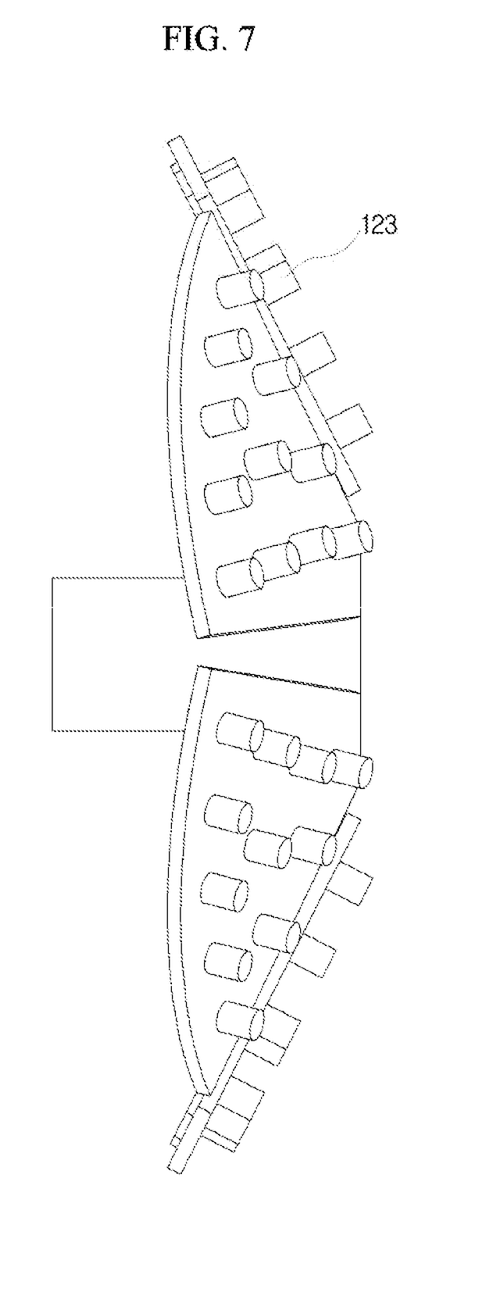
FIG. 7 is a side view illustrating a state in which an angle of the astral lamp device according to the embodiment of the present invention is controlled.

FIG. 6 is an exemplary view illustrating a state in which an angle of the LED module block of the astral lamp device according to the embodiment of the present invention is controlled, and FIG. 7 is a side view illustrating a state in which an angle of the astral lamp device according to the embodiment of the present invention is controlled.

An angle control part 150 according to the embodiment of the present invention receives an angle control command signal, and transmits a driving signal to a motor connected to the LED module block 120 in response to the angle control command.

The motor controls an angle of the LED module block 120 based on the driving signal, and controls an angle formed between the LED module block 120 and an virtual line vertically passing through a center of the central frame 110.

In another embodiment, an angle of the LED module block 120 may be controlled based on an operation state of a component disposed on the astral lamp head.

For example, the angle may be controlled by an operation state of a sterilization rod which is a component disposed on the astral lamp head. For example, the user may manually roll (rotate) the sterilization rod so that the angle of the LED module block may be controlled. In another example, the user may manually pull up the sterilization rod so that the angle of the LED module block may be controlled.

Thus, the astral lamp device having the detachable and angle-controllable LED module blocks controls the angle of the LED module blocks 120, and thus, an irradiation range may be easily controlled based on a size of a wound.

The astral lamp device having the detachable and angle-controllable LED module blocks may preferably further include an image photographing part configured to photograph an event occurring in the illuminating range of the LED module block 120, a storage part configured to store the photographed event, and a communication part configured to transmit the photographed event to a preset device.

Here, the communication part may wirelessly transmit the image data of the event (surgery progress) occurring in the illumination range to a tablet PC, a PC, or a cellular phone, and thus, the progress of the surgery may be checked from the outside in real time.

Figure 8:
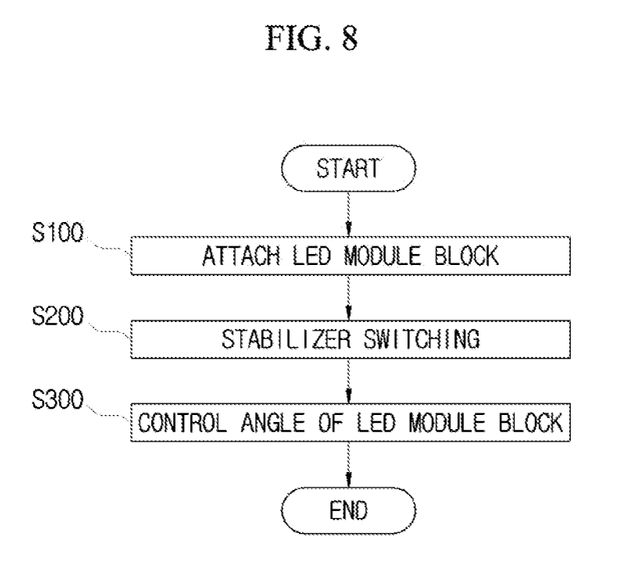
FIG. 8 is a flowchart illustrating a method of setting an astral lamp device according to an embodiment of the present invention when stabilizer switching is included.

FIG. 8 is a flowchart illustrating a method of setting an astral lamp device according to an embodiment of the present invention when stabilizer switching is included.

As illustrated in FIG. 8, when stabilizer switching according to the embodiment of the present invention is included, the method of setting the astral lamp device includes attaching one ends of a plurality of LED module blocks on a central frame (S100), switching a stabilizer based on the number of the LED module blocks attached to the central frame (S200), and controlling an angle of the LED module block (S300).

In S100, a detachable interface disposed on the one end of the LED module block is connected to the central frame to attach the LED module block. Here, the LED module block is a detachable block, and includes the detachable interface configured to connect the central frame to the LED module block, LED modules, and heat dissipation parts.

In S200, information of the number of the LED module blocks to be attached to the central frame is received, and the LED module block is connected to a preset stabilizer.

For example, in S200, the four LED modules are attached to the central frame in S100, and when one LED module block is 15 W the stabilizer is switched to a 60 W stabilizer among previously prepared stabilizers, which corresponds to the four LED module blocks.

That is, S200 corresponds to a variation in the output in response to the change in the number of the LED module blocks, and switches the stabilizer to the stabilizer corresponding to the above.

The method of setting the astral lamp device according to the embodiment of the present invention is a method using the LED module blocks which individually include stabilizers, but since the astral lamp device may be used by attaching the above LED module block to the central frame without the stabilizer switching in S100, the above S200 may be omitted.

In S300, an angle control command signal is input, and a driving signal is transmitted to a motor connected to the LED module block in response to the angle control command, and thus, an angle is formed between the LED module block and an virtual line vertically passing through a center of the central frame.

That is, in S300, the angle of the LED module block may be controlled based. on the input angle control command signal, and an irradiation range may be controlled based on the size of the wound.

In another embodiment, in S300, the angle of the LED module block may be controlled based on an operation state of a component disposed on an astral lamp head. For example, the user may manually roll (rotate) the sterilization rod so that the angle of the LED module block may be controlled, and as an example, the user may manually pull up the sterilization rod so that the angle of the LED module block may be controlled.

The method of setting the astral lamp according to the embodiment of the present invention, after S300, may preferably farther include photographing and storing the event, occurring in the illumination range of the TED module block, and the image data of the event (surgery progress) occurring in the illumination range may be wirelessly transmitted to a tablet PC, a PC, or a cellular phone, and thus, the progress of the surgery may be checked from the outside in real time.

The astral lamp device having detachable and angle-controllable LED module blocks and a method of setting the same according to the embodiment of the present invention is different from a conventional LED astral lamp, since the LED module blocks may be individually detachable, a broken or depleted LED module block may be individually replaced, and thus, the astral lamp device can be transformed into an astral lamp conforming to the economic and environmental circumstances of a user.

When the maximum possible installment numbered LED module blocks fill are initially installed in a central frame, an initial cost may be more increased, and thus, the astral lamp device can use a smaller number (for example, three) of LED module blocks than the maximum possible number (for example, eight), and additional LED module blocks may be bought by necessity to increase the number of the LED module blocks, and thus, can have an economical effect.

Since stabilizers may be provided with respect to output of the LED module blocks, a stabilizer can be switched to a stabilizer corresponding to the output based on the change in the number of the LED module blocks.

In another embodiment of the present invention, an individual stabilizer may be disposed on each of the LED module blocks, and thus, the LED module block can be detachable without switching.

Also, an angle of the LED module block may be controlled using a motor installed in the LED module block, and the angle of the LED module block may be controlled by a button input signal of the user, or a structure configured to manually control the angle of the LED module block directly by the user (for example, the angle of the LED module block may be controlled by rolling a sterilization rod disposed on a center of an astral lamp head), and thus, a desired illumination range can be easily controlled based on the size of the wound.

An individual heat dissipation structure provided on each LED module block can increase the heat dissipation effect, and an outer frame provided can securely install the LED module blocks in the astral lamp.

An individual dimming system may be prepared on each LED module block, and thus, the luminance of the LED astral lamp can be controlled based on the circumstances of a surgery.

The effect of the present invention should not be limited to the above description, and other effects which were not described will be understood by the person skilled in the art based on the claims below.

Up to now, this disclosure has focused on the preferred embodiments of the present invention. One of ordinary skill in the art will appreciate that the present invention can be implemented in a modified form without departing from essential characteristics of the invention. Therefore, the exemplary embodiments should be considered in a descriptive sense only and not for purposes of limitation. The scope of the invention is defined in the claims rather than the foregoing description, and thus various changes made in these exemplary embodiments without departing from the scope of the invention claimed by the claims and their equivalents are to be construed as being included in the present invention.

What is claimed is:

1. An astral lamp device comprising:
   a plurality of light emitting diode (LED) module blocks respectively having first ends detachably coupled to and disposed on a central frame;
   an angle control part configured to control an angle of each of the plurality of LED module blocks coupled to the central frame; and
   a switching part configured to switch to one of a plurality of stabilizers in response to a setting signal, the setting signal indicating a number of the coupled LED module blocks, the switched one of the plurality of stabilizers having a preset amount of power that corresponds to the number of the coupled LED module blocks.

2. The device of claim 1, wherein each of the LED module blocks comprises:
   a detachable interface configured to connect the central frame to each of the LED module blocks;
   at least one LED module; and
   at least one heat dissipation part of the LED module.

3. The device of claim 2, wherein the at least one heat dissipation part is disposed in a direction opposite to an illumination direction of the at least one LED module with respect to a body of each of the LED module blocks.

4. The device of claim 1, wherein the angle control part controls an angle formed between each of the LED module blocks and a virtual line vertically passing through a center of the central frame based on an operation state of a component disposed on the central frame.

5. The device of claim 1, further comprising an outer frame connected to second ends of the LED module blocks to support the LED module blocks.

6. The device of claim 1, wherein the switched one of the plurality of stabilizers has a preset wattage as the preset amount of power corresponding to the number of the coupled LED module blocks.

7. The device of claim 1, wherein the switching part comprises:
   a setting part configured to receive the setting signal indicating the number of the coupled LED module blocks;
   the plurality of stabilizers having a plurality of preset amounts of power that respectively correspond to a plurality of numbers of a plurality of LED module blocks; and
   a switch configured to connect the setting part to the switched one of the plurality of stabilizers.

8. The device of claim 7, wherein the setting part generates a switching signal based on the setting signal, and
   wherein the switch comprises a plurality of switches respectively coupled to the plurality of stabilizers, the switched one of the plurality of stabilizers being selected in response to the switching signal.

9. The device of claim 1, wherein the plurality of stabilizers respectively have a plurality of preset amounts of power, the plurality of preset amounts of power being multiples of a power of each of the LED module blocks.

10. A method of setting an astral lamp device comprising:
    detachably coupling first ends of a plurality of LED module blocks to a central frame; and
    controlling an angle of each of the plurality of LED module block,
    switching to one of a plurality of stabilizers in response to a setting signal, the setting signal indicating a number of the coupled LED module blocks, the switched one of the plurality of stabilizers having a preset amount of power that corresponds to the number of the coupled LED module blocks.

11. The method of claim 10, wherein the coupling includes connecting a detachable interface disposed on the first ends of the LED module blocks to the central frame.

12. The method of claim 10, wherein the switched one of the plurality of stabilizers has a preset wattage as the preset amount of power corresponding to the number of the coupled LED module blocks.

13. The method of claim 10, wherein the controlling includes controlling an angle formed between each of the LED module blocks and a virtual line vertically passing through a center of the central frame based on an operation state of a component disposed on the central frame.

14. The method of claim 10, wherein a plurality of switches are respectively coupled to the plurality of stabilizers, the method further comprising:
    generating a switching signal based on the setting signal; and
    selecting the switched one of the plurality of stabilizers in response to the switching signal.

15. The method of claim 10, wherein the plurality of stabilizers respectively have a plurality of preset amounts of power, the plurality of preset amounts of power being multiples of a power of each of the LED module blocks.

* * * * *